United States Patent
Sikela

(10) Patent No.: US 9,988,681 B2
(45) Date of Patent: Jun. 5, 2018

(54) DIAGNOSIS AND PROGNOSIS OF SEVERITY OF AUTISM SPECTRUM DISORDERS

(71) Applicant: James M. Sikela, Centennial, CO (US)

(72) Inventor: James M. Sikela, Centennial, CO (US)

( * ) Notice: Subject to any disclaimer, the term of this patent is extended or adjusted under 35 U.S.C. 154(b) by 296 days.

(21) Appl. No.: 14/576,092

(22) Filed: Dec. 18, 2014

(65) Prior Publication Data
US 2015/0167090 A1 Jun. 18, 2015

Related U.S. Application Data

(60) Provisional application No. 62/059,135, filed on Oct. 2, 2014, provisional application No. 61/917,910, filed on Dec. 18, 2013.

(51) Int. Cl.
*C12Q 1/68* (2018.01)

(52) U.S. Cl.
CPC .......... *C12Q 1/6883* (2013.01); *C12Q 1/686* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,143,496 A | 11/2000 | Brown et al. | |
| 8,535,889 B2 | 9/2013 | Larson et al. | |
| 2011/0301050 A1 | 12/2011 | Pfeifer et al. | |
| 2013/0172206 A1 | 7/2013 | Uddin et al. | |

OTHER PUBLICATIONS

Davis ("Copy number variation, head circumference and features of autism spectrum disorder" University of Colorado Health Sciences Center, ProQuest Dissertations Publishing 2011).*
Hegele (Arterioscler Throm Vasc Biol 2002 vol. 22 pp. 1058-1061).*
Lucentini (The Scientist 2004 vol. 18 pp. 1-3).*
U.S. Appl. No. 14/422,083, filed Feb. 17, 2015, Sikela.
Bostrom et al., "Cognitive Enhancement: Methods, Ethics, Regulatory Challenges," Sci. Eng. Ethics 2009, vol. 15 pp. 311-341 (31 pages).
Brunetti-Pierri et al., "Recurrent reciprocal 1q21.1 deletions and duplications associated with microcephaly or macrocephaly and developmental and behavioral abnormalities," Nat. Genet., 2008, vol. 40(12), pp. 1466-1471 (15 pages).
Davis et al., "Mode of Genetic Inheritance Modifies the Association of Head Circumference and Autism-Related Symptoms: A Cross Sectional Study," PLoS One, 2013, vol. 8(9), 8 pages.
Dumas et al., "DUF1220 Domains, Cognitive Disease, and Human Brain Evolution," Cold Spring Harbor Symposia on Quantitative Biology, 2009, vol. 74, pp. 375-382 (9 pages).
Dumas et al., "DUF1220—Domain Copy Number Implicated in Human Brain-Size Pathology and Evolution," American Journal of Human Genetics, 2012, vol. 91, pp. 1-11.
Dumas et al., "Gene copy number variation spanning 60 million years of human and primate evolution," Cold Spring Harbor Laboratory Press, 2007, vol. 17, pp. 1266-1277.
Dumas et al., Supplemental Data, "DUF1220—Domain Copy Number Implicated in Human Brain-Size Pathology and Evolution," American Journal of Human Genetics, 2012, vol. 91, pp. 1-19.
Gebhard, "Genome-wide analysis of aberrant CpG island methylation in human tumors," Dissertation, University of Regensburg, Jan. 2010, 180 pages.
Hindson et al., "High-Throughput Droplet Digital PCR System for Absolute Quantitation of DNA Copy Number," Anal. Chem., 2011, vol. 83(22), pp. 8604-8610.
Keeney et al., "DUF1220 protein domains drive proliferation in human neural stem cells and are associated with increased cortical volume in anthropoid primates," Brain. Struct. Funct., 2014, (abstract only).
Kenworthy et al., "Adaptive Behavior Ratings Correlate with Symptomatology and IQ Amoung Individuals with High-Functioning Autism Spectrum Disorders," J. Autism. Dev. Disord., 2010, vol. 40(4), pp. 416-423 (14 pages).
Lajonchere, "Changing the Landscape of Autism Research: The Autism Genetic Resource Exchange," Neuron, 2010, vol. 68(2), pp. 187-191 (9 pages).
Li et al., "Integrated systems analysis reveals a molecular network underlying autism spectrum disorders," Molecular Systems Biology, 2014, vol. 10, pp. 1-17.
O'Bleness et al., "Evolutionary History and Genome Organization of DUF1220 Protein Domains," Genes/Genomes/Genetics, 2012, vol. 2(9), pp. 977-986 (10 pages).
O'Bleness et al., "Finished sequence and assembly of the DUF1220-rich 1q21 region using a haploid human genome," BMC Genomics, 2014, vol. 15, p. 387 (12 pages).
Popesco et al., "Human Lineage-Specific Amplification, Selection, and Neuronal Expression of DUF1220 Domains," Science, 2006, vol. 313, pp. 1304-1307 (5 pages).
Ya et al., "Accelerated head growth in early development of individuals with autism," Pediatr Neurol, 2005, vol. 32, pp. 102-108, (abstract only).
Yeo et al., "Rare Copy Number Deletions Predict Individual Variation in Intelligence," PLoS One, 2011, vol. 6(1), pp. 1-8.
Yu et al., "Dimension reduction and mixed-effects model for microarray meta-analysis of cancer," Front Biosci. J. Virtual Libr., 2008, vol. 13, pp. 2714-2720, (abstract only).
Zhang, "Inferring polymorphism-induced regulatory gene networks active in human lymphocyte cell lines by weighted linear mixed model analysis of multiple RNA-Seq datasets," PLoS One, 2013, 8(10), 12 pages.

(Continued)

*Primary Examiner* — Amanda Haney
(74) *Attorney, Agent, or Firm* — Sheridan Ross P.C.

(57) ABSTRACT

Methods of predicting the level of symptom severity in individuals with autism spectrum disorders (ASD) that may include autism disorder, Asperger syndrome, and pervasive developmental disorder not otherwise specified. Therapeutic methods of delivering DUF1220 domain CON1 subtype domain protein products or fragments or mimetics thereof or antagonists thereof to treat ASD or ameliorate symptoms of ASD in an individual.

3 Claims, No Drawings

(56) References Cited

OTHER PUBLICATIONS

International Search Report and Written Opinion for International (PCT) Application No. PCT/US2013/055194, dated Jan. 30, 2014, 12 pages.
International Preliminary Report on Patentability for International (PCT) Application No. PCT/US2013/055194, dated Feb. 17, 2015, 8 pages.
Pennisi "A Closer Look at SNPs Suggests Difficulties," Science, Sep. 18, 1998, vol. 281, No. 5384, pp. 1787-1789.

* cited by examiner

SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Synthetic Primer

<400> SEQUENCE: 1
aatgtgccat cacttgttca aatag                                    25

<210> SEQ ID NO 2
<211> LENGTH: 27
<212> TYPE: DNA
<213> ORGANISM: Artificial Sequence
<220> FEATURE:
<223> OTHER INFORMATION: Synthetic Primer

<400> SEQUENCE: 2
gactttgtct tcctcaaatg tgatttt                                  27

<210> SEQ ID NO 3
<211> LENGTH: 26
<212> TYPE: DNA
<213> ORGANISM: Artificial Sequence
<220> FEATURE:
<223> OTHER INFORMATION: Synthetic Primer

<400> SEQUENCE: 3
catggccctt atgactccaa ccagcc                                   26

<210> SEQ ID NO 4
<211> LENGTH: 23
<212> TYPE: DNA
<213> ORGANISM: Artificial Sequence
<220> FEATURE:
<223> OTHER INFORMATION: Synthetic Primer

<400> SEQUENCE: 4
gctgttcaag acaactggaa gga                                      23

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
gggagctgct ggaggtagt                                           19

```
<210> SEQ ID NO 6
<211> LENGTH: 26
<212> TYPE: DNA
<213> ORGANISM: Artificial Sequence
<220> FEATURE:
<223> OTHER INFORMATION: Synthetic Primer

<400> SEQUENCE: 6
agagcctgaa gtcttgcagg actcac                                    26

<210> SEQ ID NO 7
<211> LENGTH: 18
<212> TYPE: DNA
<213> ORGANISM: Artificial Sequence
<220> FEATURE:
<223> OTHER INFORMATION: Synthetic Primer

<400> SEQUENCE: 7
gatttggacc tgcgagcg                                             18

<210> SEQ ID NO 8
<211> LENGTH: 18
<212> TYPE: DNA
<213> ORGANISM: Artificial Sequence
<220> FEATURE:
<223> OTHER INFORMATION: Synthetic Primer

<400> SEQUENCE: 8
gcggctgtct ccacaagt                                             18

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
ttctgacctg aaggctctgc gc                                        22
```

DIAGNOSIS AND PROGNOSIS OF SEVERITY OF AUTISM SPECTRUM DISORDERS

CROSS REFERENCE TO RELATED APPLICATION

This application claims the benefit of priority under 35 U.S.C. § 119(e) to U.S. Provisional Patent Application Ser. No. 61/917,910, filed Dec. 18, 2013, and U.S. Provisional Patent Application Ser. No. 62/059,135, filed Oct. 2, 2014. The entire contents of each of the foregoing applications is incorporated herein by reference.

TECHNICAL FIELD

The invention relates to methods of estimating the severity of social impairment in an individual diagnosed with autism by evaluating DUFF1220 domain copy number in the individual's DNA.

BACKGROUND OF THE DISCLOSURE

DUF1220 Domain

DUF1220 is a protein domain of unknown function that shows a striking human lineage-specific (HLS) increase in copy number and is associated with human brain evolution. DUF1220 domains are approximately 65 amino acids in length and are encoded by a two-exon doublet. In the human genome, DUF1220 sequences are located primarily on chromosome 1 in region 1q21.1-q21.2, with several copies also found at 1p36, 1p13.3, and 1p12. Sequences encoding DUF1220 domains show signs of positive selection, especially in primates, and are expressed in several human tissues including brain, where their expression is restricted to neurons.

The copy number of the DUF1220 domain increases as a function of a species evolutionary proximity to humans. DUF1220 copy number is highest in humans, having over 270 copies, with person-to-person variations in copy number, and shows the largest HLS increase in copy number (an additional 160 copies) of any protein coding region in the human genome. DUF1220 copy number is reduced in African great apes (estimated 125 copies in chimpanzees), further reduced in orangutan (92) and Old World monkeys (35), single- or low-copy in non-primate mammals and absent in non-mammals.

Autism Spectrum Disorders (ASDs)

ASDs are a group of developmental disabilities that can cause significant social, communication and behavioral challenges. ASDs are "spectrum disorders" that affect each person in different ways, and can range from very mild to severe. People with ASDs share some similar symptoms, such as problems with social interaction. But there are differences in when the symptoms start, how severe they are, and the exact nature of the symptoms.

There are three different types of ASDs:

1) Autistic Disorder (also called "classic" autism)

People with autistic disorder usually have significant language delays, social and communication challenges, and unusual behaviors and interests. Many people with autistic disorder also have intellectual disability.

2) Asperger Syndrome

People with Asperger syndrome usually have some milder symptoms of autistic disorder. They might have social challenges and unusual behaviors and interests. However, they typically do not have problems with language or intellectual disability.

3) Pervasive Developmental Disorder—Not Otherwise Specified (PDD-NOS; also called "atypical autism")

People who meet some of the criteria for autistic disorder or Asperger syndrome, but not all, may be diagnosed with PDD-NOS. People with PDD-NOS usually have fewer and milder symptoms than those with autistic disorder. The symptoms might cause only social and communication challenges.

ASDs begin before the age of 3 and last throughout a person's life, although symptoms may improve over time. Some children with ASD show hints of future problems within the first few months of life. In others, symptoms might not show up until 24 months or later. Some children with ASD seem to develop normally until around 18 to 24 months of age and then they stop gaining new skills, or they lose the skills they once had.

Head circumference has also been implicated in degree of impairment in affected individuals, such that increased head circumference is associated with increasing symptom severity (Davis J M, Keeney J G, Sikela J M, Hepburn S (2013) Mode of Genetic Inheritance Modifies the Association of Head Circumference and Autism-Related Symptoms: A Cross-Sectional Study. PLoS ONE 8:e74940. doi: 10.1371/journal.pone.0074940). However, the opposite association has also been found (Dementieva Y A, Vance D D, Donnelly S L, et al (2005) Accelerated head growth in early development of individuals with autism. Pediatr Neurol 32:102-108. doi: 10.1016/j.pediatrneurol.2004.08.005), which suggests a complex etiologic relationship with brain growth. Considering the vast clinical heterogeneity of autism presentation and that much of the phenotype is based on clinical review and parent report, it may also be expected that association studies of biological indicators, such as head circumference or various genetic markers, may not replicate across populations in different studies.

Thus, diagnosing ASDs can be difficult because there is currently no approved medical test to diagnose the disorders. Doctors look at the child's behavior and development to make a diagnosis. ASDs can sometimes be detected at 18 months or younger. By age 2, a diagnosis by an experienced professional can be considered very reliable. However, many children do not receive a final diagnosis until much older. This delay means that many children with ASD do not get the help they need.

Thus, there remains a need for a reliable medical test to predict the severity of the social impairment in an individual diagnosed with autism.

SUMMARY OF INVENTION

DUF1220 domain dosage is a key factor in the severity of the social impairment experienced by individuals diagnosed with Autism spectrum disorders (ASDs). DUF1220 domains are approximately 65 amino acids in length and have undergone rapid and extensive copy number expansion during recent primate evolution, most strikingly in the human lineage. The present inventor has developed high resolution assays to identify genomic sequences, and specifically DUF1220 copy number variations, linearly associated with each of the three primary symptoms of autism.

DUF1220 sequences exist in two distinct genomic environments: as a single (ancestral) domain in PDE4DIP (myomegalin) and as multiple tandem copies in the Neuroblastoma Breakpoint Family (NBPF) multigene family. Only the second form has undergone an evolutionarily rapid copy-number expansion.

DUF1220 domains are uniquely expanded in the human lineage such that copy number in the genome increases with increasing phylogenetic proximity to humans (Popesco M C, et al (2006) Human lineage-specific amplification, selection, and neuronal expression of DUF1220 domains. Science 313:1304-1307. doi: 10.1126/science.1127980). Reflecting this evolutionary relationship, prosimians and all non-primate mammals have fewer than 10 haploid copies, monkeys 25-35 copies, apes 90-120 copies, and humans 290 copies (O'Bleness M S, et al (2012) Evolutionary History and Genome Organization of DUF1220 Protein Domains. G3 Bethesda Md. 2:977-986. doi: 10.1534/g3.112.003061). The domains can be grouped into 6 different subtypes based on sequence similarity: conserved (CON) clades 1, 2 and 3 and human lineage specific (HLS) clades 1, 2, and 3 (Ibid). Unlike many copy number variable regions in the genome, DUF1220 domains display a Gaussian distribution in the human population, which suggests that they may mediate a broad range of phenotypic effects (Davis J M, et al (2014) DUF1220 Dosage Is Linearly Associated with Increasing Severity of the Three Primary Symptoms of Autism. PLoS Genet 10:e1004241. doi: 10.1371/journal.pgen.1004241). Increased DUF1220 CON1 copy number has been associated with increased gray matter volume in healthy individuals (Dumas L J, et al (2012) DUF1220-Domain Copy Number Implicated in Human Brain-Size Pathology and Evolution. Am J Hum Genet. doi: 10.1016/j.a-jhg.2012.07.016), incrementally increased CON2 copy number has been associated with improved cognition (Davis J M, et al (2014) DUF1220 copy number is linearly associated with increased cognitive function as measured by total IQ and mathematical aptitude scores. Hum Genet. doi: 10.1007/s00439-014-1489-2), and increased DUF1220 expression has been implicated in promoting neuronal stem cell proliferation (Keeney J G, et al (2014) DUF1220 protein domains drive proliferation in human neural stem cells and are associated with increased cortical volume in anthropoid primates. Brain Struct Funct. doi: 10.1007/s00429-014-0814-9). In the current studies, CON1 copy numbers ranged from 54 to 78 diploid copies, and HLS1 copy numbers from 125 to 257 diploid copies. The current inventor has now found in a small population (n=170) that increased copy number of CON1 had an apparent dose-response relationship with the symptoms of autism, such that with increased copy number of the CON1 subtype of DUF1220, social, communicative and repetitive behavior phenotypes each became incrementally more severe.

The present inventor's studies regarding DUF1220 domain dosage and its correlation with ASD severity suggests that modulation of the DUF1220 domain through increased or decreased expression, or by direct means of decreasing the expression products of the DUF1220 CON1 domain, or by reducing copies of DNA sequences encoding DUF1220 CON1 domains, may be useful in reducing the symptom severity in individuals with autism/ASD.

The present invention is generally related to prediction of the severity of the social impairment (e.g., the social, communicative and repetitive behavior phenotypes) an individual diagnosed with autism is predicted to have, or to develop. The present invention is also generally related to methods to identify treatments for, or preventing the development of, or identifying a subject in need of interventional treatment for, ASD.

Accordingly, one aspect of the disclosure relates to methods, and corresponding assay kits, for use in selecting an individual predicted to develop ASD. In certain embodiments, the ASD is Autistic Disorder ("classic" autism), Asperger Syndrome, Pervasive Developmental Disorder, or Multiplex Developmental Disorder (MDD). The method generally includes detecting in a DNA sample from an individual the copy number of the DUF1220 protein domain that has been discovered by the inventor to be valuable in predicting the individual's development of ASD, as well as predicting the severity of the ASD experienced by the individual.

The present inventor has studied the prognostic role of DUF1220 domain copy number and found that high DUF1220 (CON1 subtype) domain copy number directly correlates with the incidence and development of social impairment in individuals diagnosed with ASD. DUF1220 copy number increase typically occurs without a change in copy number of adjacent genes.

Based on the inventor's discoveries, a variety of tests and detection strategies are proposed, and discussed in detail below. Initially, however, the present invention includes the use of the following strategies for detection of the DUFF1220 biomarkers, alone or in various combinations: (1) detection of the level of DNA copy number or protein amplification of the (DUF1220) protein domain (i.e., DNA sequences encoding DUF1220 domains or a protein segment containing DUF1220 protein domain sequences); (2) detection of the level of DNA copy number variation for sequences encoding the DUF1220 protein domain; (3) detection of mutations in the DUF1220 domain; and, (4) detection of DUF1220 protein expression. These detection protocols may be used individually or in various combinations, and certain embodiments further include the use of various combinations of one or more biomarker detection techniques to further enhance the ability of the present method to identify individuals that may develop ASD.

The present inventor has discovered that individuals diagnosed with ASD having an increase in a specific DUF1220 domain (CON1 subtype) copy number, are predicted to have or develop a more severe form of the social impairments associated with ASDs. This relationship between DUF1220 domain (CON1 subtype) copy number and severity of ASD is linear, i.e., the greater the copy number, the greater is predicted to be the severity of the social impairment experienced or exhibited by the individual diagnosed with the ASD.

Additionally, the present inventor has discovered that in individuals with autism/ASD there is a linear relationship between the copy number of a specific DUF1220 domain (HLS1 subtype) and a lessening of the severity of the symptoms associated with the ASD. This relationship between DUF1220 domain (HLS1 subtype) copy number and severity of ASD phenotypes is therefore inverse, i.e., the greater the copy number, the less severe the symptom severity in individuals with autism/ASD.

The methods and test kits provided by the present invention are useful for predicting the severity of ASD symptoms in an individual diagnosed with autism. Such individuals might, as a result of the methods provided herein, be selected for additional monitoring or interventional treatment provided to alleviate or prevent the development or worsening of ASD symptoms. Such individuals may also, as a result of the methods provided herein, be selected for additional monitoring or interventional treatment provided to enhance or assist the development of enhanced cognitive skills.

The current invention provides methods for scaling or predicting the severity of social impairment phenotypes of ASD in an individual diagnosed with autism comprising: a) determining the level of at least one of the DUF1220 CON1 subtype and the DUF1220 HLS1 subtype in a DNA sample obtained from a patient; and b) comparing the level of the DUF1220 subtype in the DNA sample to a predetermined level of the DUF1220 CON1 subtype in a population of autistic individuals.

In certain embodiments, the method includes the detection in a sample of DNA from an individual a level of amplification (described in detail below) of the DUF1220 domain (i.e., the domain encoding DUF1220 protein). The number of copies of a DUF1220 domain in the DNA sample can be measured, for example by array comparative genomic hybridization (array CGH), in nuclei, and the protein expression can be measured, for example in immunohistochemistry assays, Western blot analysis, in cell nuclei, cytoplasm and/or membranes. In some embodiments, DUF1220 domain copy number is measured by PCR techniques, including, especially droplet digital PCR (ddPCR; Hindson, B J et al. (2011). High-throughput droplet digital PCR system for absolute quantitation of DNA copy number. Anal Chem 83(22): 8604-8610; also described in detail in U.S. Pat. No. 6,143,496, incorporated herein by reference). PCR, as well as other detection methods (e.g., FISH, immunohistochemistry), can be performed on biological samples such as sputum, bronchial lavage, ascites, spinal fluid, brain biopsy, blood (e.g. white blood cells) or other biological tissues or fluids. The markers can be measured in cell samples that are fresh, frozen, fixed or otherwise preserved.

According to the present invention, a probe (oligonucleotide probe) is a nucleic acid molecule which typically ranges in size from about 20-100 nucleotides to several hundred nucleotides to several thousand nucleotides in length. Therefore, a probe can be any suitable length for use in an assay described herein, including any length in the range of 20 to several thousand nucleotides, in whole number increments, specifically including 60-mer probe sequences. Such a molecule is typically used to identify a target nucleic acid sequence in a sample by hybridizing to such target nucleic acid sequence under stringent hybridization conditions. Hybridization conditions have been described in detail above.

PCR primers are also nucleic acid sequences, although PCR primers are typically oligonucleotides of fairly short length (e.g., 8-30 nucleotides) that are used in polymerase chain reactions. PCR primers and hybridization probes can readily be developed and produced by those of skill in the art, using sequence information from the target sequence.

In certain embodiments of methods of the disclosure, the level of DUF1220 domain amplification (the level or copy number of the DUF1220 domain) in the DNA sample is compared to a control level of DUF1220 domain selected from: (i) a control level that has been correlated with a lack or absence or decreased severity of ASD symptoms, i.e., a "normal"; and (ii) a control level that has been correlated with greater severity of ASD symptoms. According to the present invention, a "control level" is a control level of DUFF1220 domain copy number, which can include a level that is correlated with severity of symptoms of ASD.

An individual is selected as predicted to develop sever ASD symptoms, if the level of DUF1220 domain in the individual's DNA is statistically similar to, or greater than, the control level of DUF1220 domain that has been correlated with the development of severe symptoms of ASD.

It will be appreciated by those of skill in the art that a control level need not be established for each assay as the assay is performed but rather, a baseline or control value within a range of normal values can be established by referring to a form of stored information regarding a previously determined control levels for the severity of symptoms of ASD. Such a form of stored information can include, for example, but is not limited to, a reference chart, listing or electronic file of population or individual data regarding population statistics, or any other source of data regarding control DUF1220 levels that is useful for the individual to be evaluated.

In one embodiment, the method includes a step of detecting the expression of DUF1220 protein. Protein expression can be detected in suitable tissues, such as tissue and cell material obtained by biopsy. For example, the individual biopsy sample, which can be immobilized, can be contacted with an antibody, an antibody fragment, or an aptamer, that selectively binds to the protein to be detected, and determining whether the antibody, fragment thereof or aptamer has bound to the protein. Protein expression can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

In certain embodiments, the symptoms of the ASD predicted to be increased in severity by an increased copy number of the DUF1220 CON1 subtype is an increased score in the Autism Diagnostic Interview-Revised (ADI-R) social diagnostic score. In related embodiments, the symptoms of the ASD predicted to be increased in severity by an increased copy number of the DUF1220 CON1 subtype is an increased score in the Autism Diagnostic Interview-Revised (ADI-R) verbal communication diagnostic score. In related embodiments, the symptoms of the ASD predicted to be increased in severity by an increased copy number of the DUF1220 CON1 subtype is an increased score in the Autism Diagnostic Interview-Revised (ADI-R) repetitive behavior diagnostic score. In certain embodiments, the symptoms of the ASD predicted to be increased in severity by an increased copy number of the DUF1220 CON1 subtype is a decreased score in the Vineland Adaptive Behavior Scales (VABS) social standard score.

In certain embodiments, the symptoms of the ASD predicted to be decreased in severity by an increased copy number of the DUF1220 HLS1 subtype is a decreased score in the Autism Diagnostic Interview-Revised (ADI-R) verbal communication diagnostic score. In related embodiments, the symptoms of the ASD predicted to be decreased in severity by an increased copy number of the DUF1220 HLS1 subtype is an increased score in the Vineland Adaptive Behavior Scales (VABS) social standard score. In related embodiments, the symptoms of the ASD predicted to be decreased in severity by an increased copy number of the DUF1220 HLS1 subtype is an increased score in the Raven Matrices IQ test for children under 10.6 years score.

Another embodiment of the invention includes an assay kit for performing any of the methods of the present invention. The assay kit can include any one or more of the following components: (a) a means for detecting in a sample of DNA a copy number of DUF1220 domain; (b) a means for detecting in a sample of DNA the expression of DUF1220 protein; and/or (c) a means for detecting in a sample of DNA at least one (but can include more than one) mutations in the DUF1220 domain. The assay kit preferably also includes one or more controls. The controls may include: (i) a control sample for detecting low DUF1220 domain levels in an individual; (ii) a control sample for detecting high DUF1220 domain levels in an individual; (iii) information containing a predetermined control level of the DUF1220 domain. The assay kit may also include a control gene with a known copy number that can serve as an internal standard to which DUF1220 copy number measurements can be compared. The assay kit may also include means for measuring the copy number of a known gene that can serve as an internal standard to which DUF1220 copy number measurements can be compared. In a specific embodiment, the control gene is the Ribonuclease P Protein subunit p30 (RPP30) gene.

In one embodiment, a means for detecting DUF1220 domain level can generally be any type of reagent that can be used in a method of the present invention. Such a means for detecting include, but are not limited to: a probe or primer(s) that hybridizes under stringent hybridization conditions to the DUF1220 domain or a portion of chromosome 1 (the chromosome on which DUF1220 is located) or probe/primer sequences that can be used for PCR-based methods that measure DUF1220 copy number at the DNA level (for example ddPCR techniques). In a specific embodiment ddPCR is used with the following PCR Primers:

```
CON1
Left:
                                      (SEQ ID NO: 1)
AATGTGCCATCACTTGTTCAAATAG Right:
                                      (SEQ ID NO: 2)
GACTTTGTCTTCCTCAAATGTGATTTT Hyb:
                                      (SEQ ID NO: 3)
CATGGCCCTTATGACTCCAACCAGCC HLS1
Left:
                                      (SEQ ID NO: 4)
GCTGTTCAAGACAACTGGAAGGA Right:
                                      (SEQ ID NO: 5)
GGGAGCTGCTGGAGGTAGT Hyb:
                                      (SEQ ID NO: 6)
AGAGCCTGAAGTCTTGCAGGACTCAC reference (Ribonuclease P Protein
subunit p30 (RPP30))
Left:
                                      (SEQ ID NO: 7)
GATTTGGACCTGCGAGCG Right:
                                      (SEQ ID NO: 8)
GCGGCTGTCTCCACAAGT Hyb:
                                      (SEQ ID NO: 9)
TTCTGACCTGAAGGCTCTGCGC
```

Thus, in certain embodiments, these PCR primers may be included in an assay kit provided for performing methods of the present invention.

The nucleic acid sequence for the DUF1220 domain is known in the art and can be used to produce such reagents for detection. Additional reagents useful for performing an assay using such means for detection can also be included, such as reagents for performing in situ hybridization, reagents for detecting fluorescent markers, reagents for performing polymerase chain reaction, and the like.

The means for detecting in the assay kit of the present invention can be conjugated to a detectable tag or detectable label. Such a tag can be any suitable tag which allows for detection of the reagents used to detect the gene or protein of interest and includes, but is not limited to, any composition or label detectable by spectroscopic, photochemical, electrical, optical or chemical means. Useful labels in the present invention include: biotin for staining with labeled streptavidin conjugate, magnetic beads (e.g., DYNABEADS™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the means for detecting in the assay kit of the present invention can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly affecting the activity and/or ability of the detection means to detect the desired target molecule. Exemplary organic solid supports include polymers such as polystyrene, nylon, phenol-formaldehyde resins, and acrylic copolymers (e.g., polyacrylamide). The kit can also include suitable reagents for the detection of the reagent and/or for the labeling of positive or negative controls, wash solutions, dilution buffers and the like. The kit can also include a set of written instructions for using the kit and interpreting the results.

The kit may also include a means for detecting a control marker that is characteristic of the cell type being sampled, that can generally be any type of reagent that can be used in a method of detecting the presence of a known marker (at the nucleic acid or protein level) in a sample. Means for detecting a control marker include, but are not limited to: a probe that hybridizes under stringent hybridization conditions to a nucleic acid molecule encoding a protein marker; PCR primers which amplify such nucleic acid molecule; an aptamer that specifically binds to a conformationally distinct site on the target molecule; and/or an antibody, antigen binding fragment thereof, or antigen binding peptide that selectively binds to the control marker in the sample. Nucleic acid and amino acid sequences for many cell markers are known in the art and can be used to produce reagents for detection.

The assay kits and methods of the present invention can be used not only to predict the severity of the ASD symptoms in an autistic individual, but also to identify treatments that can improve cognitive function or ameliorate one or more symptoms associated with ASD and high DUFF1220 (CON1 subtype) domain levels.

The present disclosure is also concerned with methods of treating ASD in a mammal by decreasing or modulating DUF1220 CON1 expression in the mammal, or administering an inhibitor of the peptide expression products of DUF1220 CON1, or fragments thereof, or mimetics thereof, to the mammal.

The present invention is also concerned with methods for elevating the copy number of the DUF1220 domain (HLS1 subtype) in an individual.

More embodiments concern methods of screening for therapeutic agents useful in the treatment of ASD in a human comprising contacting a test compound with a polypeptide expression product of DUF1220; and detecting binding of said test compound to said polypeptide. Additional embodiments provide methods of screening for therapeutic agents useful in the treatment of ASD in a mammal comprising (a) determining the activity of any one of the polypeptides described above, at a first concentration of a test compound or in the absence of said test compound, (b) determining the activity of said polypeptide at a second concentration of said test compound, and comparing the activity of said polypeptide under conditions (a) and (b) to the activity of the polypeptide in the presence of a known regulator. In some embodiments, the activity is current.

Additional aspects concern a method for the preparation of a pharmaceutical composition useful for the treatment of ASD in a mammal comprising identifying a regulator of DUF1220 expression in the mammal, or activity of a DUF1220 peptide expression product, determining whether said regulator ameliorates the symptoms of said ASD in a mammal, and combining said regulator with an acceptable pharmaceutical carrier. In some embodiments, the regulator is a small molecule, an RNA molecule, an antisense oligonucleotide, a polypeptide, an antibody, or a ribozyme.

In another embodiment, the invention provides assays for screening candidate or test compounds that bind to or modulate the expression of DUF1220 or the functional activity of a peptide expression product of DUF1220. Such assays can employ full-length DUF1220, a biologically active fragment of DUF1220, or a fusion protein that includes all or a portion of DUF1220.

This Summary of the Invention is neither intended nor should it be construed as being representative of the full extent and scope of the present invention. Additional aspects of the present invention will become apparent from the following description and experimental findings.

DESCRIPTION OF ILLUSTRATIVE EMBODIMENTS

The present disclosure is drawn to methods of assessing DUF1220 domain copy number in an individual that can be used to predict the severity or likely severity of ASD symptoms in an individual diagnosed with ASD.
Prognostics:

One embodiment of the invention relates to a method for predicting the likelihood that an individual will have a greater likelihood of displaying or expressing symptomology associated with ASD, comprising the steps of obtaining a DNA sample from an individual to be assessed and determining the DUF1220 copy number present in the individual. The rationale behind the assay is based on the link between DUF1220 copy number and ASD symptoms/phenotype severity: in general the more copies of DUF1220 (CON1 subtype) encoded in the genome, the more likely is the likely severity of the ASD in the individual.

In a particular embodiment, the individual is an individual at risk for development of an autism disorder. In another embodiment the individual exhibits clinical symptomatology associated with an autism disorder. In one embodiment, the individual has been clinically diagnosed with an autism disorder. In certain embodiments, the test results are specifically associated with the severity of symptoms of one or more of:

1) Autistic Disorder (also called "classic" autism)
2) Autism Spectrum Disorder (ASD)
3) Asperger Syndrome, and
4) Pervasive Developmental Disorder—Not Otherwise Specified The genetic material within the individual's biological sample to be assessed can be obtained from any nucleated cell from the individual, but may also include free DNA, e.g. in blood, amniotic fluid or other human fluid. For assay of genomic DNA, virtually any biological sample (other than pure red blood cells) is suitable. For example, convenient tissue samples include whole blood, white blood cells (WBCs), semen, saliva, tears, urine, fecal material, sweat, skin and hair. Additional samples may include fetal DNA obtained from various sources, including fetal cells, amniotic fluid and maternal blood. For assay of cDNA or mRNA, the tissue sample must be obtained from an organ in which the target nucleic acid is expressed. Neural crest-derived cells include, for example, melanocytes and keratinocytes.

Many of the methods described herein require amplification of DNA from target samples. This can be accomplished by e.g., PCR. See generally: PCR Technology: Principles and Applications for DNA Amplification ed. H. A. Erlich, Freeman Press, NY, N.Y., 1992; and specifically, Hindson B J, Ness K D, Masquelier D A, et. al. (2011). High-throughput digital PCR system for absolute quantitation of DNA copy number. Anal. Chem. 83:8604-8610. Other suitable amplification methods include droplet digital PCR (ddPCR), the ligase chain reaction (LCR), transcription amplification, self-sustained sequence replication, and nucleic acid-based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Droplet Digital PCR technology is a digital PCR method utilizing a water-oil emulsion droplet system (Hindson et al., High-throughput droplet digital PCR system for absolute quantitation of DNA copy number. Anal Chem. Nov. 15, 2011; 83(22):8604-10. Epub Oct. 28, 2011; also described in U.S. Pat. No. 8,535,889, which is incorporated herein by reference). Droplets are formed in a water-oil emulsion to form partitions that separate template DNA molecules. The droplets serve the same function as individual test tubes or wells in a plate in which the PCR reaction takes place. The massive sample partitioning is a key aspect of the ddPCR technique. The droplets support PCR amplification of the template molecules they contain and use reagents and workflows similar to those used for most standard PCR assays. Following PCR, each droplet is analyzed or read in a flow cytometer to determine the fraction of PCR-positive droplets in the original sample. These data are then analyzed using Poisson statistics to determine the target DNA template concentration in the original sample.

In conducting mutation analysis, nucleotides of interest can be identified by a variety of methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE); or analysis of the DUF1220 protein. Additional methods for measuring domain copy number include ddPCR (droplet digital PCR), array comparative genomic hybridization (array CGH) and the use of DNA sequence read-depth strategies.

The methods of the present invention may be used to make the prediction of severity of ASD symptoms, independently from other information such as the individual's symptoms or the results of other clinical or paraclinical tests. However, the methods of the present invention may be used in conjunction with such other data points. Because a diagnosis is rarely based exclusively on the results of a single test, the method may be used to determine whether a subject is more likely than not to experience or display severe ASD symptoms, based on the difference between the measured and standard level or reference range of the DUF1220 domain copy number or protein products. Thus, for example, an individual with a putative diagnosis of ASD (e.g., suspected to be suffering from ASD) may be diagnosed as being "more likely" or "less likely" to display severe ASD symptoms in light of the information provided by a method of the present disclosure. In some embodiments, such difference is statistically significant.

The invention also provides a method for determining an individual's likelihood of experiencing or displaying ASD phenotypic social impairments, the method comprising obtaining a biological sample from a subject, detecting the level or activity of DUF1220 domain CON1 subtype in the DNA in the biological sample, and comparing the result to the level or activity of DUF1220 domain CON1 subtype in a sample obtained from subjects diagnosed with ASD, or to a reference range or value wherein an increase or decrease of DUF1220 domain CON1 subtype is correlated with the severity of ASD phenotypes.

In another embodiment, the invention provides methods for using the DUF1220 subtypes described herein to prognose ASD symptoms in an individual. In specific non-limiting embodiments, the methods are useful for detecting DUF1220 subtype copy numbers in DNA samples, facilitating prediction of the severity of ASD in a subject. Such methods may involve detection of levels of DUF1220 subtype copy numbers in a patient DNA sample. The detection methods of the invention may be conducted in vitro or in vivo, on isolated cells, or in whole tissues or a bodily fluid, e.g., blood, plasma, serum, urine, and the like.

The assay system can also include a means for detecting a control marker that is characteristic of the cell type being sampled and can generally be any type of reagent that can be used in a method of detecting the presence of a known marker (at the nucleic acid or protein level) in a sample, such as by a method for detecting the presence of the DUF1220 domain CON1 subtype biomarker. Specifically, the means is characterized in that it identifies a specific marker of the cell type being analyzed that positively identifies the cell type.

Another aspect of the disclosure provides methods that can be used to predict the severity of ASD symptoms of an individual having ASD. This aspect of the disclosure relates to the discovery that the copy number of the DUF1220 HLS1 domain is negatively associated with an increased ASD symptoms. Therefore, one embodiment provides a method of predicting the severity of symptoms of ASD in an individual including obtaining a biological sample from an individual, analyzing the sample for the copy number of the DUF1220 domain HLS1 subtype. Low copy number and/or protein expression/activity of DUF1220 HLS1 subtype indicates that the individual is at higher risk for developing and experiencing social impairment associated with ASD. Alternatively, high expression and/or protein function of the DUF1220 HLS1 subtype indicates that the individual is at lower risk for developing and experiencing social impairment associated with ASD.

According to the present invention, the individual being tested can be a human or non-human primate. In one embodiment, the individual being tested has been diagnosed as having ASD or is suspected of having ASD.

Therefore, one embodiment is a method for predicting that an individual diagnosed with ASD will have increased symptom severity associated with ASD comprising:
  a) obtaining a biological sample from an individual;
  b) detecting in the biological sample the presence of at least one marker selected from:
    i) the copy number of the DUF1220 domain CON1 subtype; and,
    ii) the expression or activity level of a DUF1220 domain CON1 subtype protein expression product;
    wherein the level of the at least one marker is indicative of a likelihood that the individual will have increased symptomology associated with ASD.

In this method, the biological sample may be a sample of biological fluid or a tissue sample selected from the group consisting of blood, tears, urine, saliva, skin, muscle and lymph tissue. In this method, the step of detecting may include determining the protein activity of the DUF1220 domain CON1 subtype or HLS1 protein expression products in the sample. In this method, the step of detecting may include performing at least one technique selected from the group consisting of Sanger dideoxy sequencing, pyrosequencing, other types of DNA sequencing, RNA sequencing, single-strand conformation polymorphism, heteroduplex analysis, DNA microarray technology, denaturing gradient gel electrophoresis, allele-specific PCR, Scorpion Amplification Refractory Mutation System (SARMS) technology, SNaPshot analysis of PCR products, droplet digital PCR (ddPCR), and mass spectrometry.

Another aspect is a method of identifying compounds that treat or prevent the development of ASD in a mammal by modulating the expression or activity of the DUF1220 domain CON1 or HLS1 subtypes in the mammal. Determining the ability of the test compound to bind to a membrane-bound form of DUF1220 domain can be accomplished, for example, by coupling the test compound with a radioisotope or enzymatic label such that binding of the test compound to the DUF1220 domain subtype-expressing cell can be measured by detecting the labeled compound in a complex. In a competitive binding format, the assay comprises contacting a DUF1220 expressing cell with a known compound that carries a detectable label and that binds to DUF1220 domain subtype to form an assay mixture, contacting the assay mixture with a test compound, and determining the ability of the test compound to interact with the DUF1220 expressing cell, wherein determining the ability of the test compound to interact with the DUF1220 expressing cell comprises determining the ability of the test compound to preferentially bind DUF1220 in the cell as compared to the known compound.

In another embodiment, the assay is a cell-based assay comprising contacting a cell expressing a DUF1220 (e.g., full-length DUF1220, a biologically active fragment of DUF1220, or a fusion protein that includes all or a portion of DUF1220) expressed in the cell with a test compound and determining the ability of the test compound to modulate (e.g., stimulate or inhibit) the functional activity of the DUF1220. Determining the ability of the test compound to modulate the functional activity of the DUF1220 can be accomplished by any method suitable for measuring the functional activity of DUF1220, e.g., any method suitable for measuring the activity. The activity can be measured in a number of ways, not all of which are suitable for any given target protein.

These methods may also include the use of cell-free assays. Such assays involve contacting a form of DUF1220 (e.g., full-length DUF1220, a biologically active fragment of DUF1220, or a fusion protein comprising all or a portion of DUF1220) with a test compound and determining the ability of the test compound to bind to DUF1220. Binding of the test compound to DUF1220 can be determined either directly or indirectly as described above. In one embodiment, the assay includes contacting DUF1220 with a known compound that carries a detectable label and that binds DUF1220 to form an assay mixture, contacting the assay mixture with a test compound, and determining the ability of the test compound to interact with DUF1220, wherein determining the ability of the test compound to interact with DUF1220 comprises determining the ability of the test compound to preferentially bind to DUF1220 as compared to the known compound.

In various embodiments of the above assay methods of the present invention, it may be desirable to immobilize DUF1220 (or a DUF1220 target molecule) to facilitate separation of complexed from uncomplexed forms of one or both of the proteins, as well as to accommodate automation of the assay. Binding of a test compound to DUF1220, or interaction of DUF1220 with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase (GST) fusion proteins can be adsorbed onto glutathione sepharose beads or glutathione derivatized microtiter plates, which are then combined with the test compound or the test compound and either the non-adsorbed target protein or DUF1220, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of DUF1220 can be determined using standard techniques.

Other techniques for immobilizing proteins on matrices can also be used in the screening assays of the invention. For example, either DUF1220 or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, IU.), and immobilized in the wells of streptavidin-coated plates (Pierce Chemical). Alternatively, antibodies reactive with DUF1220 or target molecules but that do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with DUF1220 or target molecule, as well as enzyme-linked assays that rely on detecting an enzymatic activity associated with DUF1220 or target molecule.

The screening assays can also involve monitoring the expression of DUF1220. For example, regulators of expression of DUF1220 domain CON1 subtype can be identified in a method in which a cell is contacted with a candidate compound and the expression of DUF1220 protein or mRNA in the cell is determined. The level of expression of DUF1220 protein or mRNA in the presence of the candidate compound is compared to the level of expression of DUF1220 protein or mRNA in the absence of the candidate compound. The candidate compound can then be identified as a regulator of expression of DUF1220 based on this comparison. For example, when expression of DUF1220 protein or mRNA protein is greater (statistically significantly greater) in the presence of the candidate compound than in its absence, the candidate compound is identified as a stimulator of DUF1220 protein or mRNA expression. Alternatively, when expression of DUF1220 protein or mRNA is less (statistically significantly less) in the presence of the candidate compound than in its absence, the candidate compound is identified as an inhibitor of DUF1220 protein or mRNA expression. The level of DUF1220 protein or mRNA expression in the cells can be determined by methods well known in the art.

Gene Expression:

In another embodiment, test compounds that increase or decrease DUF1220 domain expression are identified. As used herein, the term "correlates with expression of a polynucleotide" indicates that the detection of the presence of nucleic acids, the same or related to a nucleic acid sequence encoding DUF1220, by northern analysis or real-time PCR is indicative of the presence of nucleic acids encoding DUF1220 in a sample, and thereby correlates with expression of the transcript from the polynucleotide encoding DUF1220. The term "microarray", as used herein, refers to an array of distinct polynucleotides or oligonucleotides arrayed on a substrate, such as paper, nylon or any other type of membrane, filter, chip, glass slide, or any other suitable solid support. A DUF1220 polynucleotide is contacted with a test compound, and the expression of an RNA or polypeptide product of DUF1220 polynucleotide is determined. The level of expression of appropriate mRNA or polypeptide in the presence of the test compound is compared to the level of expression of mRNA or polypeptide in the absence of the test compound. The test compound can then be identified as a regulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

Such screening can be carried out either in a cell-free assay system or in an intact cell. Any cell that expresses DUF1220 polynucleotide can be used in a cell-based assay system. The DUF1220 polynucleotide can be naturally occurring in the cell or can be introduced into the cell. Either a primary culture or an established cell line can be used.

Methods of Use:

The present invention provides for both prophylactic and therapeutic methods for treating ASD, including ameliorating the symptoms of ASD, in a mammal.

The modulatory methods involve contacting a cell with an agent that modulates one or more of the activities of DUF1220 domain CON1 or HLS1 subtype. An agent that modulates activity can be an agent as described herein, such as a nucleic acid or a protein (including the DUF1220 domain protein), a naturally-occurring cognate ligand of the polypeptide, a peptide, a peptidomimetic, or any small molecule. In one embodiment, the agent stimulates one or more of the biological activities of DUF1220. In another embodiment, the agent inhibits one or more of the biological activities of DUF1220. As such, the present invention provides methods of treating an individual afflicted with a disease or disorder characterized by unwanted expression or activity of DUF1220 or a protein expression product of DUF1220. In one embodiment, the method involves administering an agent like any agent identified or being identifiable by a screening assay as described herein, or combination of such agents that may upregulate or downregulate the expression or activity of DUF1220 or of any protein expression product of DUF1220. In another embodiment, the method involves administering a regulator of DUF1220 as therapy to compensate for increased or undesirably high expression or activity of DUF1220 or a protein expression product of DUF1220.

Inhibition of activity or expression of DUF1220 is desirable in situations in which activity or expression of DUF1220 is abnormally high and in which decreasing its activity is likely to have a beneficial effect.

Another aspect is a method of modulating expression and/or activity of the DUF1220 protein in a mammal to increase cognitive function in the mammal, to improve motor function, to improve memory and learning abilities, to reduce depression and anxiety, and/or to treat, ameliorate, or prevent ASD in a mammal. Preferably, the mammal in these embodiments is a human. A specific embodiment is the use of a DUF1220 domain CON1 subtype protein antagonist in the manufacture of a medicament for the treatment of ASD in a human. A related embodiment is the use of a pharmaceutical composition comprising DUF1220 domain CON1 subtype protein antagonist in the preparation of a medicament for the treatment of ASD or the enhancement of cognitive function in a human. Another specific embodiment is a pharmaceutical composition comprising DUF1220 protein for use in the treatment of ASD or the enhancement of cognitive function in a human. Another embodiment is a method of treating ASD or enhancing cognitive function in an individual comprising administering an effective amount of DUF1220 domain CON1 subtype protein antagonist to an individual in need thereof. Another embodiment is a method of treating an individual suffering from, or at risk of developing ASD or low cognitive function comprising administering an effective amount of a DUF1220 domain CON1 subtype protein antagonist to the individual in need thereof.

Pharmaceutical Compositions:

This invention further pertains to isolated proteins or novel agents identified by the above-described screening assays and uses thereof for the therapeutic uses described above. The active agents (also referred to herein as "active compounds") of the invention can be incorporated into pharmaceutical compositions suitable for administration. Such compositions typically comprise the active agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a regulator of DUF1220 domain CON1 subtype expression or activity (and/or a regulator of the activity or expression of a protein in the DUF1220 signaling pathway) as well as methods for preparing such compositions by combining one or more such regulators and a pharmaceutically acceptable carrier.

An antagonist of DUF1220 domain CON1 subtype may be produced using methods that are known in the art. In particular, purified DUF1220, or polypeptides corresponding to all or part of the DUF1220 domain, may be used to produce antibodies or to screen libraries of pharmaceutical agents to identify those that specifically bind DUF1220. Antibodies to DUF1220 may also be generated using methods that are well known in the art. Such antibodies may include, but are not limited to, polyclonal, monoclonal, chimeric, single chain antibodies, Fab fragments, and fragments produced by a Fab expression library.

In another embodiment, the polynucleotides encoding DUF1220, or any fragment or complement thereof, may be used for therapeutic purposes. In one aspect, the complement of the polynucleotide encoding DUF1220 may be used in situations in which it would be desirable to block the transcription of the DUF1220 mRNA. In particular, cells may be transformed with sequences complementary to polynucleotides encoding DUF1220. Thus, complementary molecules or fragments may be used to modulate DUF1220 activity, or to achieve regulation of gene function. Such technology is now well known in the art, and sense or antisense oligonucleotides or larger fragments can be designed from various locations along the coding or control regions of sequences encoding DUF1220.

Any of the therapeutic methods described above may be applied to any subject in need of such therapy, including, preferably, humans.

A related embodiment is the administration of a pharmaceutical composition containing DUF1220 in conjunction with a pharmaceutically acceptable carrier, for any of the therapeutic effects discussed above. Such pharmaceutical compositions may constitute DUF1220, antibodies to DUF1220, and mimetics, agonists, antagonists, or inhibitors of DUF1220. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The Examples, which follow, are illustrative of specific embodiments of the invention, and various uses thereof. They are set forth for explanatory purposes only, and are not to be taken as limiting the invention.

EXAMPLES

Example 1

The inventor has linked increasing copy number of DUF1220 domain subtype CON1 to increasing severity of primary symptoms of autism. In this study, the inventor carried out a replication study in which DNA samples were obtained from a different autism population. The data indicate that the new results (this Replication study conducted on 288 Autism Cases) that were obtained closely matched the original study (the original study conducted on 183 Autism Cases) with respect to increasing CON1 copy number being associated with increasing severity of impaired social reciprocity in individuals with autism. In other words, as CON1 copy number increased in individuals with autism, impaired social reciprocity became incrementally worse.

ddPCR was used to measure CON1 copy number, as described herein and O'Bleness M, et al (2014) Finished sequence and assembly of the DUF1220-rich 1q21 region using a haploid human genome. BMC Genomics 15:387. doi: 10.1186/1471-2164-15-387. Associations (correlations) were examined between CON1 copy number and phenotype severity within cases. The main measure of severity for autism from ADI-R that the inventor tested was impaired social reciprocity.

The results demonstrated that CON1 copy number increase correlated with increased severity of impaired social reciprocity. In individuals with autism, for each copy increase of CON1, the severity of impaired social reciprocity increased 0.25 units (on a scale of 6 to 30); Beta=0.25 (original study 0.24); SE=0.11 (original study 0.11); p=0.021 (original study 0.036). This example provides additional evidence that, in individuals with autism (autism spectrum disorder), increasing copy number of DUF1220 subtype CON1 is linearly associated with increasing severity of impaired social reciprocity.

Example 2

Increased DUF1220 CON1 copy number has been associated with increased gray matter volume in healthy individuals (Dumas L J, et al (2012) DUF1220-Domain Copy Number Implicated in Human Brain-Size Pathology and Evolution. Am J Hum Genet. doi: 10.1016/j.ajhg.2012.07.016), incrementally increased CON2 copy number has been associated with improved cognition (Davis J M, et al (2014) DUF1220 copy number is linearly associated with increased cognitive function as measured by total IQ and mathematical aptitude scores. Hum Genet. doi: 10.1007/s00439-014-1489-2), and increased DUF1220 expression has been implicated in promoting neuronal stem cell proliferation (Keeney J G, et al (2014) DUF1220 protein domains drive proliferation in human neural stem cells and are associated with increased cortical volume in anthropoid primates. Brain Struct Funct. doi: 10.1007/s00429-014-0814-9). Given these findings, the inventor hypothesized in previous work that CON1 would be associated with symptoms of autism and would exhibit a similar incremental gene dosage effect. The inventor found in a small population (n=170) that increased copy number of CON1 had an apparent dose-response relationship with the symptoms of autism, such that with increased copy number of the CON1 subtype of DUF1220, social, communicative and repetitive behavior phenotypes each became incrementally more severe (Davis J M, et al (2014) DUF1220 Dosage Is Linearly Associated with Increasing Severity of the Three Primary Symptoms of Autism. PLoS Genet 10:e1004241. doi: 10.1371/journal.pgen.1004241).

The inventor sought to replicate those findings in an independent sample as replication studies in complex conditions are important and serve as a level of validation. It should also be noted, however, that lack of replication is also informative, and may suggest important yet subtle differences between populations reflecting the broad heterogeneity of complex neurodevelopmental conditions.

166 non-Hispanic white, primarily multiplex individuals with autism or autism spectrum as classified by the Autism Diagnostic Observations Schedule (ADOS), and with Vineland Adaptive Behavior Scales (VABS) social standardized scores above 20 were selected for replication studies. 144 of these individuals had IQ scores available. The Autism Diagnostic Observation Schedule was used as an enrollment mechanism and children diagnosed with autism or autism spectrum disorder were included. Higher functioning multiplex individuals were preferentially selected due to previous evidence suggesting the most pronounce effects of DUF1220 CON1 copy number would be identifiable in this group (Davis J M, et al (2014) DUF1220 Dosage Is Linearly Associated with Increasing Severity of the Three Primary Symptoms of Autism. PLoS Genet 10:e1004241. doi: 10.1371/journal.pgen.1004241). Non-Hispanic white individuals were selected to control for population stratification.

Droplet digital PCR (ddPCR), a third generation PCR technique, was used to assay CON1 and HLS1 copy number as previously described (O'Bleness M, et al (2014) Finished sequence and assembly of the DUF1220-rich 1q21 region using a haploid human genome. BMC Genomics 15:387. doi: 10.1186/1471-2164-15-387).

Sequences of the primers used were:

```
CON1
Left:
                                            (SEQ ID NO: 1)
AATGTGCCATCACTTGTTCAAATAG Right:
                                            (SEQ ID NO: 2)
GACTTTGTCTTCCTCAAATGTGATTTT Hyb:
                                            (SEQ ID NO: 3)
CATGGCCCTTATGACTCCAACCAGCC HLS1
Left:
                                            (SEQ ID NO: 4)
GCTGTTCAAGACAACTGGAAGGA Right:
                                            (SEQ ID NO: 5)
GGGAGCTGCTGGAGGTAGT Hyb:
                                            (SEQ ID NO: 6)
AGAGCCTGAAGTCTTGCAGGACTCAC
```

-continued reference (Ribonuclease P Protein
subunit p30 (RPP30))
Left:
                                            (SEQ ID NO: 7)
GATTTGGACCTGCGAGCG Right:
                                            (SEQ ID NO: 8)
GCGGCTGTCTCCACAAGT Hyb:
                                            (SEQ ID NO: 9)
TTCTGACCTGAAGGCTCTGCGC Autism symptom scores were taken from the Autism Diagnostic Interview—Revised (ADI-R), the VABS, and the Raven Progressive Matrixes (RPM). All DNA was obtained from cell lines from the Rutgers branch of the Autism Genetic Resource Exchange (Lajonchere C M (2010) Changing the Landscape of Autism Research: The Autism Genetic Resource Exchange. Neuron 68:187-191. doi: 10.1016/j.neuron.2010.10.009). All DNA assays were conducted in a blinded randomized manner to guard against differential misclassification.

Assays were conducted on 96 well plates and despite high reproducibility (r>0.9) variability from plate to plate exists, such that subtle correlations exist within plates and variability exists between plates. To accommodate this and to more precisely calculate standard errors and beta estimates, the inventor utilized mixed models with maximum likelihood estimation with a random intercept for plate similar to previous work (Yu T, et al (2008) Dimension reduction and mixed-effects model for microarray meta-analysis of cancer. Front Biosci J Virtual Libr 13:2714-2720; Zhang W, (2013) Inferring polymorphism-induced regulatory gene networks active in human lymphocyte cell lines by weighted linear mixed model analysis of multiple RNA-Seq datasets. PloS One 8:e78868. doi: 10.1371/journal.pone.0078868). Each sample was nested within plate to account for the experimental design in all regression analyses. Akike Information Criterion suggested a marked improved model fit in HLS1 cognitive analyses and was uninformative in CON1 analyses. Covariates sex, age, head circumference, HLS1, and RPM IQ were explored in all models. Reduced models, including CON1, were developed through backwards selection. Covariates that remained in the ADI-R Social Score analysis were CON1 (p=0.036) and IQ (p=0.02). CON1 (p=0.07), and HLS1 (p=0.046) remained in the ADI-R communication analysis. The VABS analysis included CON1 (p=0.11), HLS1 (p=0.02), IQ (p=0.005), and age (p<0.001). Even though CON1 did not universally meet a strict alpha of less than 0.05 it was left in models to explore trending effects (see Tablet). IQ investigations explored effects stratified by mean age group (<10.6) due to previous findings that cognitive effects of DUF1220 may be most pronounced in males younger than 11 (Davis J M, et al (2014b) DUF1220 copy number is linearly associated with increased cognitive function as measured by total IQ and mathematical aptitude scores. Hum Genet. doi: 10.1007/s00439-014-1489-2). HLS1 was the only significant covariate in the IQ analyses. R version 3.0.2 (cran.r-project.org/) with the nlme package (Bates D, et al Development Core Team (2011) Linear and nonlinear mixed effects models (nlme)) was used for analyses.

In the population of 166 non-Hispanic white individuals with autism, CON1 copy number ranged from 54 to 78 diploid copies, and HLS1 copy number from 125 to 257 diploid copies. The copy number of each clade followed a Gaussian distribution in this population (Table 1).

TABLE 1

| Full Population Characteristics (n = 168) | | | | | |
|---|---|---|---|---|---|
| Characteristic | Proportion | $1^{st}$ quartile | mean | median | $3^{rd}$ quartile |
| Sex (Male) | 79.8% | | | | |
| Multiplex | 96.4% | | | | |
| Age | | 7.8 | 10.6 | 9.9 | 12.5 |
| ADOS Classification (Autism, Autism Spectrum) | 69.1%, 31.0% | | | | |
| ADI-R Social Diagnostic Score | | 16.0 | 20.2 | 21.0 | 25.0 |
| ADI-R Verbal Communication Diagnostic Score | | 13.0 | 16.4 | 17.0 | 20.0 |
| ADI-R Repetitive Behaviors Diagnostic Score | | 4.0 | 6.1 | 6.0 | 8.0 |
| VABS Social Standard Score | | 53.0 | 64.1 | 64.0 | 74.0 |
| Raven Matrices IQ (n = 144) | | 93.2 | 100 | 100 | 110 |
| CON1 Copy Number | | 63 | 66 | 66 | 69 |
| HLS1 Copy Number | | 185 | 198 | 196 | 209 |

Previously, the inventor identified a similar distribution of CON1 copy number ranging from 56 to 88 copies (Davis J M, et al (2014) DUF1220 Dosage Is Linearly Associated with Increasing Severity of the Three Primary Symptoms of Autism. PLoS Genet 10:e1004241. doi: 10.1371/journal.pgen.1004241) and found an association between increased copies of CON1 and increased Autism Diagnostic Interview—Revised (ADI-R) Social Diagnostic Score (p=0.036), as found in the original investigation (Table 2). With each additional copy of CON1, Social Diagnostic Score increased 0.24 points (SE=0.11), becoming progressively more severe. The inventor also identified trends between increased CON1 copies and both increased ADI-R Verbal Communicative Diagnostic Score and decreased Vineland Adaptive Behavior Scales (VABS) Social Adaptive Score that were similar to the initial investigation (Table 2).

TABLE 2

| Adjusted CON1 Social Diagnostic Score Replication | | | |
|---|---|---|---|
| CON1 associations | beta | SE | p-value |
| ADI-R Social Diagnostic Score, Study1* | 0.25 | 0.11 | 0.021 |
| ADI-R Social Diagnostic Score, Study2 | 0.24 | 0.11 | 0.036 |
| ADI-R Verbal Communication Diagnostic Score, Study 1* | 0.18 | 0.08 | 0.030 |
| ADI-R Verbal Communication Diagnostic Score, Study 2 | 0.16 | 0.09 | 0.072 |
| ADI-R Repetitive Behavior Diagnostic Score, Study 1* | 0.10 | 0.05 | 0.047 |
| ADI-R Repetitive Behavior Diagnostic Score, Study 2 | 0.00 | 0.05 | 1.0 |
| VABS Social Standard Score, Study 1* | −0.43 | 0.23 | 0.056 |
| VABS Social Standard Score, Study 2 | −0.38 | 0.26 | 0.143 |

*Davis JM, Searles VB, Anderson N, et al (2014a) DUF1220 Dosage Is Linearly Associated with Increasing Severity of the Three Primary Symptoms of Autism. PLoS Genet 10: e1004241. doi: 10.1371/journal.pgen.1004241

The inventor also investigated potential associations between HLS1 copy number and autism-related symptoms. HLS domains represent an attractive candidate for influencing neurologic symptoms as they account for much of the unique and extreme expansion of DUF1220 copy number between humans and non-human primates. Approximately 149 copies of HLS-type DUF1220 domain sequences have been added to the human genome since divergence from chimpanzee (O'Bleness et al 2014). Using ddPCR with HLS1-specific primers the inventor identified protective associations between increased HLS1 copy number and autism-like symptoms. Increased copy number of HLS1 was associated with improved Social Adaptive Score as measured from the VABS (p=0.02), improved ADI-R Verbal Communicative Diagnostic Score (p=0.046), and a progressively increased IQ in children younger than 10.6 (n=80) as measured by the Raven Matrices (p=0.02)(Table 3). The IQ association was not identified in the original population. However, characteristics of this study's group are subtly different, which could affect this association.

TABLE 3

Adjusted HLS1 Associations from the Current Study

| HLS1 associations | beta | SE | p-value |
| --- | --- | --- | --- |
| ADI-R Verbal Communication Diagnostic Score | −0.04 | 0.02 | 0.046 |
| VABS Social Standard Score | 0.14 | 0.06 | 0.023 |
| Raven Matrices IQ in children younger than 10.6 years | 0.19 | 0.08 | 0.025 |

These data provide a replication of previous findings that there is a linear association between CON1 copy number and progressively more impaired Social Diagnostic Score as measured by the ADI-R. This association, implicating DUF1220 dosage in the severity of a primary autism phenotype, has therefore been validated in two independent populations of individuals with autism. Considering the vast heterogeneity of the condition and that the characterizations of these phenotypes are largely driven by parent report and behavioral evaluations, these replicated findings substantiate the idea that DUF1220 CON1 copy number may modulate social symptoms in autistic individuals. Notably, the beta effects of CON1 show highly similar trends across social and communicative metrics. Even though CON1 was not significant in the communication analysis, the fact that the beta values were highly similar, with similar standard errors suggests that with a larger study the association with communication score may be significant. The analysis of CON1 versus Social Adaptive Score from the VABS also detected similar beta effects and standard errors between studies, which would also suggest that in a larger study these may be significant as well. The association previously reported between CON1 copy number and severity of repetitive behaviors did not replicate here. This may indicate a spurious result in the initial analysis or may indicate that there are important differences, perhaps unmeasured, between these populations that affect the association between CON1 and repetitive behavior symptom severity.

Autism is remarkably heterogeneous and different covariates were important in these investigations. This may suggest that these populations are subtly different. Importantly, after adjustment, the effect of CON1 is independent of other predictors of the condition and further implicates CON1 as having a specific role in autism-related social ability. Previous investigations suggested that CON1 effects are most important in multiplex individuals, and this investigation demonstrated the same association. These findings suggest that the role of CON1 may be most important in relatively higher functioning individuals with autism. As previous CNV-related genomic studies have focused on rare, larger scale events in individuals with simplex autism who have been identified with markedly lower IQ the role of common variation of CON1 in multiplex children represents a promising novel direction in autism research. Expanding genomic efforts to target more functional children beyond simplex-based investigations is also important given that a large portion of children with autism have IQs above 70.

The social ability measured in these studies is heavily reliant on parent report. Although the ADI-R is a clinical gold standard, continued improvement of social metrics will refine the assessment of the condition and precise associations between social functioning and CON1 copy number may be further clarified. Future investigations of CON1 in exceptionally well-phenotyped populations with additional social measures such as the Social Response Score or perhaps a latent social phenotype will also better elucidate the relationship between CON1 and autism-related social symptoms.

The inventor also identified an opposite association between HLS1 copy number and autism symptoms, such that increased copies of HLS1 were associated with improved symptoms. These findings were not seen in the original population and remain to be replicated. The lack of replication could be due to different population characteristics between the studies and the sample size available. The original work identified the most pronounced CON1 social effect in multiplex individuals. Stratification in that analysis reduced the effective sample size by half giving 85 multiplex individuals for multiplex specific analyses. This would have decreased power to detect lesser effects of HLS1 that may be most pronounced in multiplex individuals as well. This study aimed to replicate the inventor's original findings by examining a larger sample of mostly (96%) multiplex children, and found a protective relationship of HLS1 with autism communication symptoms and Raven's Progressive Matrices (RPM) IQ. The cognitive findings are consistent with previous analyses of DUF1220 in typically developing youths however, which demonstrated that increases in copy number of CON2 were significantly associated with increased Wechsler Intelligence Scale for Children (WISC) IQ and increases in HLS1 trended towards increased WISC IQ (Davis et al 2014a). Future investigations with larger samples of multiplex children may replicate associations that suggest a protective relationship of HLS1 copy number and autism related symptoms.

Unraveling the exact nature of these relationships will require both more precise phenotyping and more thorough investigations of DUF1220 copy number change localization in the genome. ddPCR, the assay tool utilized in this study, produces a global genomic estimate of copy number but is unable to localize copy number changes to specific Neuroblastoma Breakpoint Family (NBPF) genes. As there are no differences in global DUF1220 copy number between individuals with autism and those typically developing (Davis J M, et al (2014a) DUF1220 Dosage Is Linearly Associated with Increasing Severity of the Three Primary Symptoms of Autism. PLoS Genet 10:e1004241. doi: 10.1371/journal.pgen.1004241), it is possible that localizing DUF1220 copy number increases and decreases to specific NBPF genes may identify additional associations with autism etiology and phenotype severity. Further, the fact that the relationship between CON1 and communication score was nearly significant after adjusting for HLS1 suggests a complex relationship among DUF1220 domain subtype dosage variations and autism related symptoms, and perhaps etiology. As technologies improve, the identification of gene-specific and domain-specific events could shed light on any causal mechanisms DUF1220 domains may have on autism.

This represents the first replication of a gene dosage relationship with the severity of a primary symptom of autism. This is an important and unique effect given the broad range of severity presented in individuals with autism, and represents an exciting novel direction of genetic research in the condition.

The foregoing examples of the present disclosure have been presented for purposes of illustration and description. Furthermore, these examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A method of assessing the predicted severity of impaired social reciprocity and/or a score in the Autism Diagnostic Interview-Revised (ADI-R) social diagnostic score for a human subject having an Autism Spectrum Disorder (ASD) comprising:
   a) obtaining a DNA sample from a human individual diagnosed with ASD
   b) detecting in the DNA sample by Droplet Digital PCR quantification a copy number of DUF1220 CON1 subtype that is between 54 and 88; and
   c) predicting severity of impaired social reciprocity and/or a score in the Autism Diagnostic Interview-Revised (ADI-R) social diagnostic score for the human individual diagnosed with ASD, wherein the higher the copy number of DUF1220 CON1 subtype is, the more likely the human individual diagnosed with ASD will have an increased severity of impaired social reciprocity and/or an increased score in the Autism Diagnostic Interview-Revised (ADI-R) social diagnostic score.

2. The method of claim 1, wherein the DNA sample is obtained from a blood sample from the individual diagnosed with ASD.

3. The method of claim 1, wherein the individual diagnosed with ASD is a multiplex ASD individual.

* * * * *

UNITED STATES PATENT AND TRADEMARK OFFICE
CERTIFICATE OF CORRECTION

PATENT NO.        : 9,988,681 B2
APPLICATION NO.   : 14/576092
DATED             : June 5, 2018
INVENTOR(S)       : James M. Sikela It is certified that error appears in the above-identified patent and that said Letters Patent is hereby corrected as shown below:

In the Claims

Column 25, Line 47, Claim 1 replace "subject having" with --individual diagnosed with--

Signed and Sealed this
Tenth Day of July, 2018

Andrei Iancu
*Director of the United States Patent and Trademark Office*